(12) United States Patent
Diller et al.

(10) Patent No.: US 11,141,076 B1
(45) Date of Patent: Oct. 12, 2021

(54) THERMALLY ACTIVATED NON-INVASIVE BLOOD PERFUSION MEASUREMENT SYSTEMS

(71) Applicants: Thomas Eugene Diller, Blacksburg, VA (US); Ali Reza Roghanizad, Blacksburg, VA (US); Brian Vick, Blacksburg, VA (US); Tim O'Brien, Blacksburg, VA (US)

(72) Inventors: Thomas Eugene Diller, Blacksburg, VA (US); Ali Reza Roghanizad, Blacksburg, VA (US); Brian Vick, Blacksburg, VA (US); Tim O'Brien, Blacksburg, VA (US)

( * ) Notice: Subject to any disclaimer, the term of this patent is extended or adjusted under 35 U.S.C. 154(b) by 41 days.

(21) Appl. No.: 15/435,260

(22) Filed: Feb. 16, 2017

Related U.S. Application Data (60) Provisional application No. 62/295,657, filed on Feb. 16, 2016.

(51) Int. Cl.
| | |
|---|---|
| *A61B 5/26* | (2021.01) |
| *A61B 5/026* | (2006.01) |
| *A61B 5/0205* | (2006.01) |
| *A61B 5/01* | (2006.01) |

(52) U.S. Cl.
CPC .......... *A61B 5/026* (2013.01); *A61B 5/02055* (2013.01); *A61B 5/015* (2013.01); *A61B 2560/0238* (2013.01); *A61B 2562/028* (2013.01); *A61B 2562/0285* (2013.01)

(58) Field of Classification Search
CPC ..................................................... A61B 5/026
See application file for complete search history.

(56) References Cited

U.S. PATENT DOCUMENTS

| | | | | |
|---|---|---|---|---|
| 4,926,867 | A * | 5/1990 | Kanda ................ | A61B 5/14552 600/334 |
| 7,040,805 | B1 * | 5/2006 | Ou ......................... | G01N 25/72 250/341.6 |
| 2004/0236225 | A1 * | 11/2004 | Murphy ................ | A61B 5/015 600/473 |
| 2012/0190967 | A1 * | 7/2012 | Nahm ................... | A61B 6/504 600/411 |
| 2016/0135686 | A1 * | 5/2016 | Gencer ................ | A61B 5/0093 |

OTHER PUBLICATIONS

Alkhwaji, Abdusalam, Brian Vick, and Tom Diller. "New mathematical model to estimate tissue blood perfusion, thermal contact resistance and core temperature." Journal of biomechanical engineering 134.8 (2012): 081004. (Year: 2012).*

Mudaliar, Ashvinikumar V., et al. "A phantom tissue system for the calibration of perfusion measurements." Journal of biomechanical engineering 130.5 (2008): 051002. (Year: 2008).*

(Continued)

*Primary Examiner* — Daniel L Cerioni
*Assistant Examiner* — Yasmeen S Warsi
(74) *Attorney, Agent, or Firm* — Johnston Holroyd; Mary-Jacq Holroyd (57) ABSTRACT

A sensor system for measuring blood perfusion, blood temperature, and thermal resistance using heat transfer and temperature measurements. The system uses a heat flux sensor, temperature sensor and electric resistance heater with a data analysis device using measurements before, during and after the thermal event provided by the heater.

17 Claims, 5 Drawing Sheets

(56) References Cited

OTHER PUBLICATIONS

Baker, K. I. (1993). Unsteady surface heat flux and temperature measurements (Doctoral dissertation, Virginia Tech). (Year: 1993).*

A. Alkhwaji, B. Vick, and T. Diller, "New mathematical model to estimate tissue blood perfusion, thermal contact resistance and core temperature.," J. Biomech. Eng., vol. 134, No. 8, p. 81004-1-81004-8, Aug. 2012.

"Standard Test Method for Measuring Heat Flux Using Surface-Mounted One-Dimensional Flat Gages," Designation: E2684-17, ASTM International.

H. H. Pennes, "Analysis of Tissue and Arterial Blood Temperatures in the Resting Human Forearm", J. of Applied Physiology, vol. 1, No. 2, 1948.

F.A. Castellana, R. Skalak, J. M. Cho, and R. B. Case, "Steady-State Analysis and Evaluation of a New Thermal Sensor for Surface Measurements of Tissue Perfusion," Annals of Biomedical Engineering, vol. 11, pp. 101-115, 1983.

Tze-Yuan Cheng, Cila Herman, "Analysis of skin cooling for quantitative dynamic infrared imaging of near-surface lesions," International Journal of Thermal Sciences 86, 175e188, 2014.

G. Holti and K. W. Mitchell, "Estimation of the Nutrient Skin Blood Flow Using a Non-Invasive Segmented Thermal Clearance Probe," Royal Victoria Infirmary, Newcastle upon Tyne, England.

H. J. Li,1 X. X. Zhang,1, 2 and Y. F. Yi, "Measurement of Blood Perfusion Using the Temperature Response to Constant Surface Flux Heating", International Journal of Thermophysics, vol. 23, No. 6, Nov. 2002.

J. Okajima, T. Okabe, T. Sugiura, A. Komiya, T. Seki, and S. Maruyama, "Estimation of Blood Perfusion Rate and its Temperature Dependency in Human Abdominal Area Under Heating Condition," Proceedings of the 15th International Heat Transfer Conference, IHTC—15, Aug. 10-15, 2014.

P. A. Patel, J. W. Valvano, J. A. Pearce, S.A. Prahl, and C. R. Denham, "A Self-Heated Thermistor Technique to Measure Effective Thermal Properties From the Tissue Surface," Transactions of the ASME, Journal of Biomechanical Engineering, vol. 109, pp. 330-335, Nov. 1987.

Abdusalam Al-Khwaji, Brian Vick, and Tom Diller, "Modeling and Estimating Simulated Burn Depth Using the Perfusion and Thermal Resistance Probe," Journal of Medical Devices, ASME, vol. 7 / 031003-1-9, Sep. 2013.

* cited by examiner

THERMALLY ACTIVATED NON-INVASIVE BLOOD PERFUSION MEASUREMENT SYSTEMS

RELATED APPLICATIONS

This application claims the benefit of U.S. Provisional Application Ser. No. 62/295,657 entitled "Thermally Activated Non-Invasive Blood Perfusion Measurement Systems" filed on Feb. 16, 2016, the contents of which are incorporated herein by reference in its entirety.

COPYRIGHT NOTICE

A portion of the disclosure of this patent document may contain material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

Blood perfusion, defined as the fluid exchange rate through a given volume or mass of tissue (in units of ml/ml/s or ml/100 g/min), is important for normal tissue physiology and is part of the temperature regulatory system of the body. Changes in blood perfusion are also associated with a variety of pathologic processes. For example, the assessment of shock progression or peripheral vascular disease would be greatly improved with quantitative blood perfusion data.

Perfusion can be estimated from following the transfer of thermal energy in the body by using model-based parameter estimation methods. This requires both a thermal mathematical model of the system, along with a model-based minimization method to estimate perfusion. The most widely used thermal model for living tissue approximation was developed by Pennes (1948). Here, energy loss due to blood flow is accounted for by including a perfusion term in the conduction heat transfer equation. The resulting expression is commonly referred to as the Pennes BioHeat Transfer Equation (BHTE).

$$(\rho c)_t \frac{\partial T}{\partial t} = k_t \nabla^2 T + (\rho c \omega)_b (T_a - T) \tag{1}$$

Here, the properties $\rho$, c, and k, are the local density, specific heat and thermal conductivity; T is the local temperature, $T_a$ is the arterial temperature, t is time, $\omega$ is the local perfusion, the subscripts t and b refer to tissue and blood, and metabolic heat generation is assumed negligible.

Although systems have been tried using thermal events to infer blood perfusion (Castallena, et al., 1983; Holti and Mitchell, 1979; Li et al., 2002; Okajima, et al., 2014; Patel et al., 1987; Cheng and Herman, 2014), they've had little success because the amount of heat transfer into the tissue must be inferred than rather directly measured.

There are several possible methods to solve equation 1 matching the results with experimental data. One basic solution method is given by Alkhwaji et al. (2012). In terms of the variable $\theta(x, t) = T(x, t) - T_{core}$ the bio-heat equation (Pennes, 1948) is $$\rho C \frac{\partial \theta}{\partial t} = k \frac{\partial^2 \theta}{\partial x^2} - (\rho C w)_b \theta \tag{3}$$

The assumptions are one-dimensional heat flow, constant properties matching blood and tissue, and negligible internal heat generation. The blood perfusion is $w_b$, the thermal conductivity is k, the density is $\rho$, and the specific heat is C. The tissue is assumed to be semi-infinite in extent, giving the far boundary condition as $$\left. \frac{\partial \theta}{\partial x} \right|_{x \to \infty} = 0 \tag{4}$$

At the surface of the tissue (x=0) the heat flux must match that through the thermal contact resistance, R". The measured surface temperature ($\theta_s$) gives the second boundary condition $$-k \left. \frac{\partial \theta}{\partial x} \right|_{x=0} = \frac{1}{R''} (\theta_S(t) - \theta(0, t)) \tag{5}$$

Before the thermal event is initiated, the temperature distribution in the tissue is assumed to be at steady state.

$$\theta(x,0) = \theta_i(x) \tag{6}$$

For this case the heat flux at the surface is balanced by the warming effects of the blood perfusion in the tissue. The resulting tissue temperature distribution is $$\theta_i(x) = \theta_{S,0} \left[ \frac{1}{1 + R'' k \sqrt{w_b/\alpha}} \right] e^{-\sqrt{w_b/\alpha}\, x} \tag{7}$$

This specifies the initial condition for the transient solution. The corresponding initial heat flux at the surface is $$q_i(x=0) = -k\theta_{S,0} \left[ \frac{\sqrt{w_b/\alpha}}{1 + R'' k \sqrt{w_b/\alpha}} \right] \tag{8}$$

which is defined as positive from the tissue to the sensor.

The solution for the transient case, which starts with implementation of the thermal event is accomplished by using the Green's function method. The result is a closed-form analytical solution which is the sum of all the step changes in temperature starting from time $t_1$ until $t_{max}$. The complete solution is the addition of this with the initial temperature distribution. The corresponding total heat flux is found using the transient temperature evaluated at the surface of the tissue $$q_S = \frac{\theta(0, t) - \theta_S(t)}{R''} \tag{9}$$

with $q_s$ defined as positive from the tissue. This is used to match with the experimentally measured values.

Figure 2A:
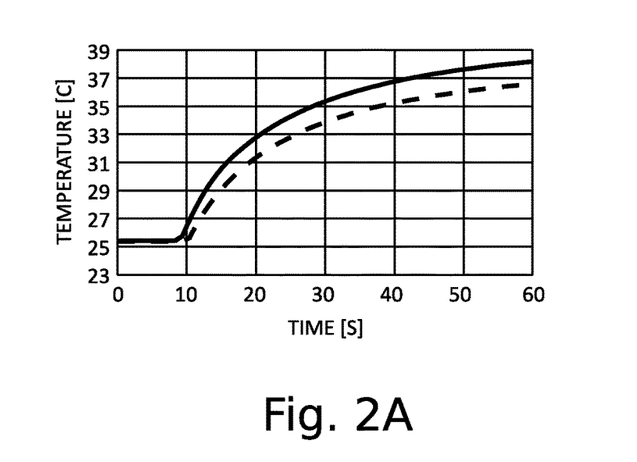
FIGS. 2A and 2B show measured and analytical values of temperature (FIG. 2A) and heat flux (FIG. 2B) of first device.
Figure 2B:
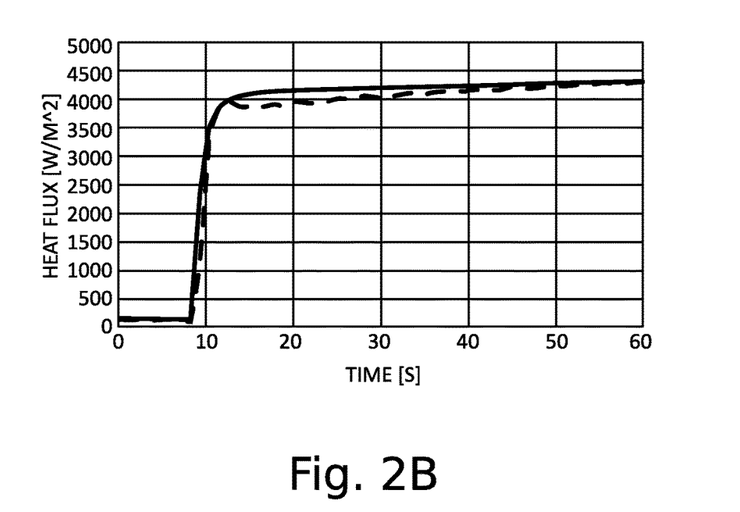

An example of the measured and analytical values is shown in the FIG. 2. The reason for the offset of the surface tissue (analysis) and sensor (measured) temperatures is due to the thermal contact resistance of R''=0.000368 m²-K/W between the sensor and the tissue. The measured and analytical heat flux matches quite well, as determined by the parameter estimation. The fit between the model and data is quantified using the average square root of the squared residual values $$S = \sqrt{\frac{1}{N_{max}} \sum_{n=1}^{N_{max}} r_n^2} \qquad (10)$$

where the residual is $$r_n = q_{s,n} - q_{Analytical,n} \qquad (11)$$

The best fit of the analytical model to the measurements is when the value of S is the minimum value, which is the best estimate of the parameters. This gives the appropriate values of blood perfusion, blood temperature and thermal contact resistance.

SUMMARY OF THE INVENTION

The present invention relates to practical devices that use heat flux and temperature measurements at the surface of tissue before and during thermal events to determine the tissue blood perfusion. The theory and mathematics of the method have been established and openly published (Alkhwaji et al, 2012). The devices require measurements of both the surface heat flux and temperature as a function of time along with signal processing and analysis to determine the local blood perfusion, the local blood temperature and the thermal contact resistance at the surface of the tissue. The design of the measurement systems and creation of the thermal events are the key to these useful devices for perfusion measurement.

Figure 1A:
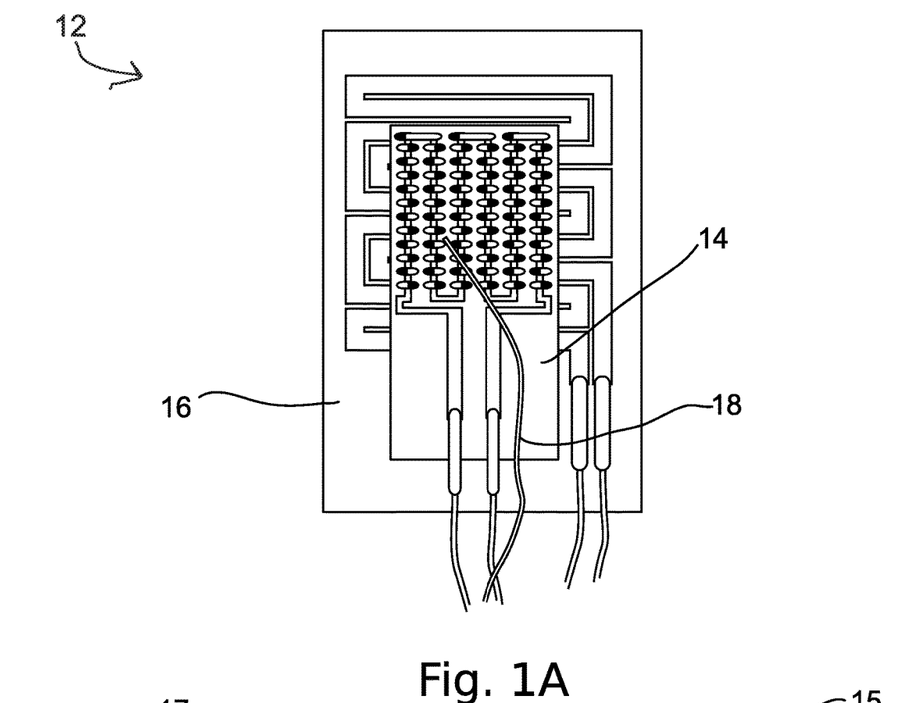
FIGS. 1A and 1B show the first perfusion sensor with the printed heat flux sensor mounted on a resistance heater.
Figure 1B:
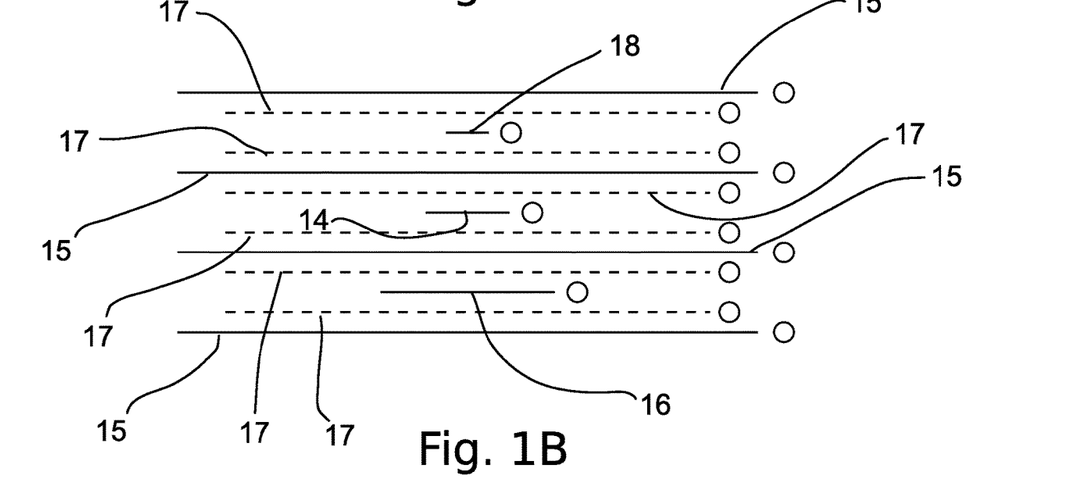

Two different devices are described that create the thermal events and collect the data to measure blood perfusion of tissue. The first is shown in FIG. 1 with a thin heat flux sensor of the type described in ASTM Standard E2684 to measure the heat flux and a thin electrical heater to create the thermal event. When not making a measurement, the sensor is passively attached to the skin with little heat flux. The measurement occurs with the imposition of a thermal event provided by the small heater mounted over the heat flux sensor. The heat flux and temperature measurements are recorded by a computer and analyzed to determine the local blood perfusion. At the end of the thermal event, which typically lasts only 60 seconds, the system comes back to equilibrium and is ready for another measurement. The process is not only painless, but also can barely be physically detected by a person undergoing the testing. One example of practical application of this device for perfusion measurements in explanted organs is shown in the paper by O'Brien et al. (2017).

The second device uses an infra-red camera to capture the temperature field of the tissue of interest as a function of time before and during a thermal event created by air blowing over the tissue. The air is used to either cool or heat the tissue with a pre-determined heat flux. A plate with heat flux sensors is used to calibrate the blown air to determine the magnitude and uniformity of the heat flux prior to the tissue measurement.

What is unique about the current systems is the direct measurement of the heat flux into the tissue with the heat flux sensor. This is a key to successful perfusion measurement, as covered in the provisional patent.

These and other aspects of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention, may best be understood with reference to the following description and accompanying drawings.

Similar reference characters denote corresponding features consistently throughout the attached drawings.

DETAILED DESCRIPTION OF PREFERRED EMBODIMENTS

The contents of the following is incorporated herein in their entirety by reference: Alkhwaji, A., Vick, B., and Diller, T. E., "New Mathematical Model to Estimate Tissue Blood Perfusion, Thermal Contact Resistance and Core Temperature," ASME Journal of Biomechanical Engineering, Vol. 134, 2012, 081004. The following article by the inventors is attached as an appendix. The contents of which is incorporated into the present application explicitly by being included herein, and shows examples and the like. O'Brien, T. J., Roghanizad, A., Jones, P., Aardema, C., Robertson, J., and Diller, T. "The Development of a Thin-Filmed, Non-Invasive Tissue Perfusion Sensor to Quantify Capillary Pressure Occlusion of Explanted Organs," IEEE Transactions on Biomedical Engineering, accepted for publication.

A perfusion sensor system consisting of a deposited resistive heater and a combined heat flux sensor and temperature sensor (thermocouple) based Patent Application No. 27698375, "Heat Flux Gage" filed Dec. 5, 2016, the contents of which are incorporated herein by reference in their entirety. This system is used in conjunction with a data analysis and control device with wireless capability.

FIGS. 1A and 1B show the first perfusion sensor 12 with a printed heat flux sensor 14 mounted on a resistance heater 16 with a temperature sensor 18. FIGS. 2A and 2B show measured and analytical values of temperature (FIG. 2A) and heat flux (FIG. 2B) of first device. FIG. 1B shows the configuration of the heat flux sensor 14, the temperature sensor 18, and the electric resistance heater 16 with a mylar 15 and epoxy 17 so that the heat flux sensor 14 and temperature sensor 18 stacked with the electric resistance heater 16 as a single sensor 12.

Figure 3:
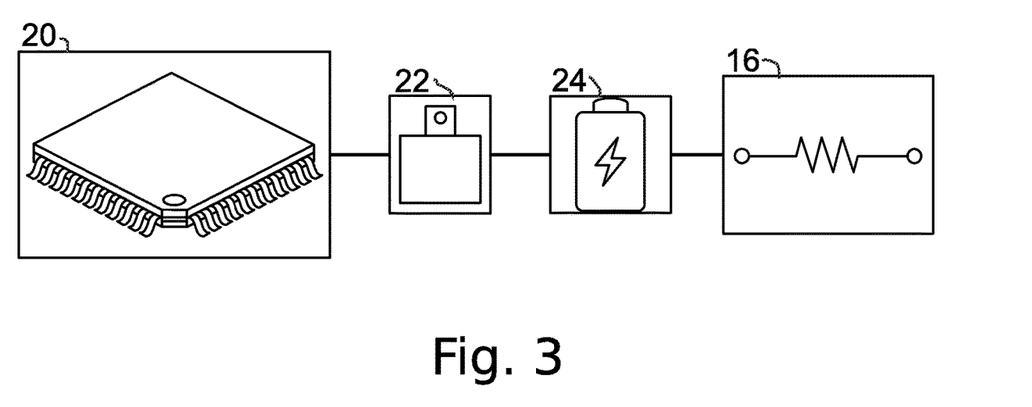
FIG. 3 shows the main control components of the Heat Flux Gage System for measuring blood perfusion, in which the heater is mounted on the backside of the heat flux sensor.

FIG. 3 shows the main control components of the heat flux gage system for measuring blood perfusion although only the heater 16 is shown. The heater 16 is mounted on the backside of the heat flux sensor 14 as shown in FIGS. 1A and 1B. A programmed data analysis device 20 (such as a stacked Arduino), a relay 22, a battery 24 are connected to the heater 16 as shown. Although not shown, the heat flux sensor 14 and temperature sensor 18 would also be attached to the programmed data analysis device 26 (or 20 and 26) adjacent the heater 16.

Figure 4A:
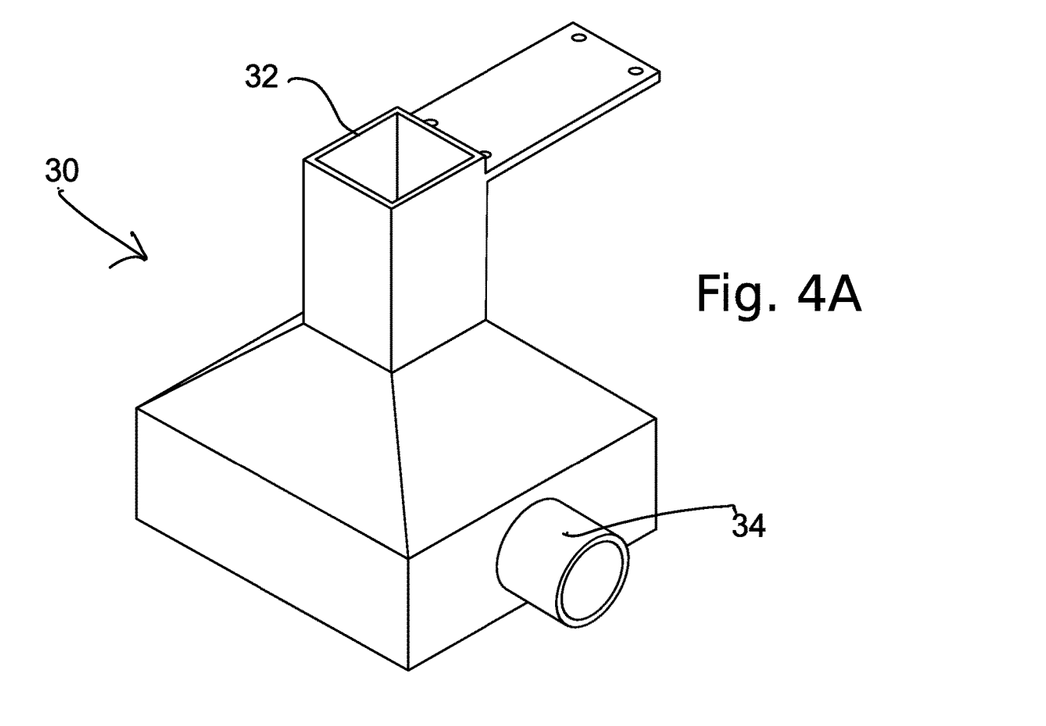
FIGS. 4A-4C shows drawings of the air supply for the IR Camera Perfusion System.
Figure 4B:
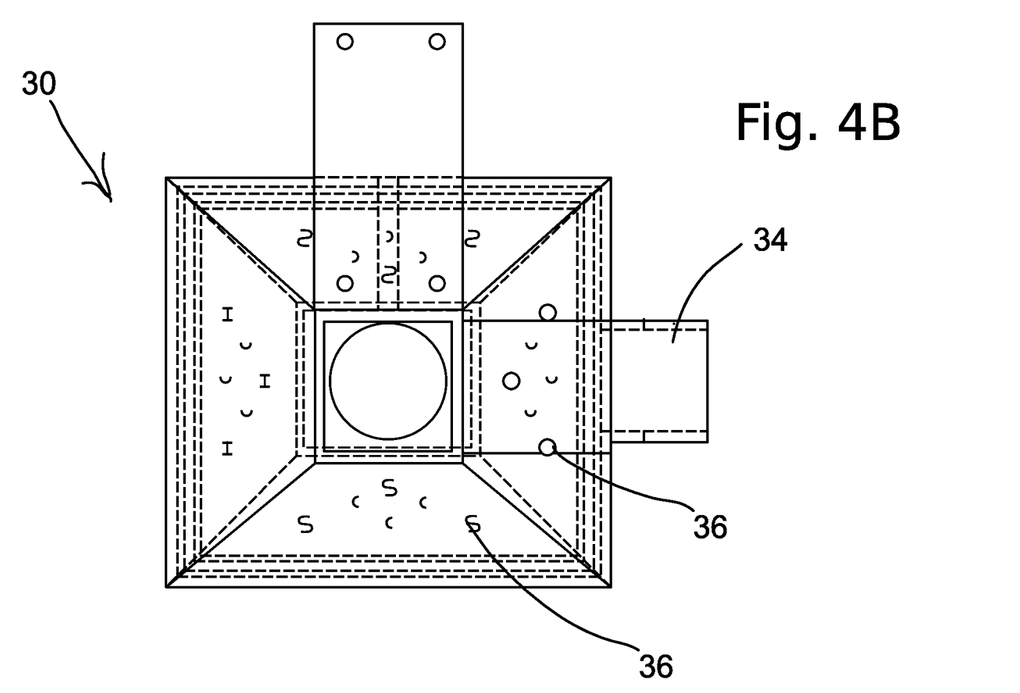
Figure 4C:
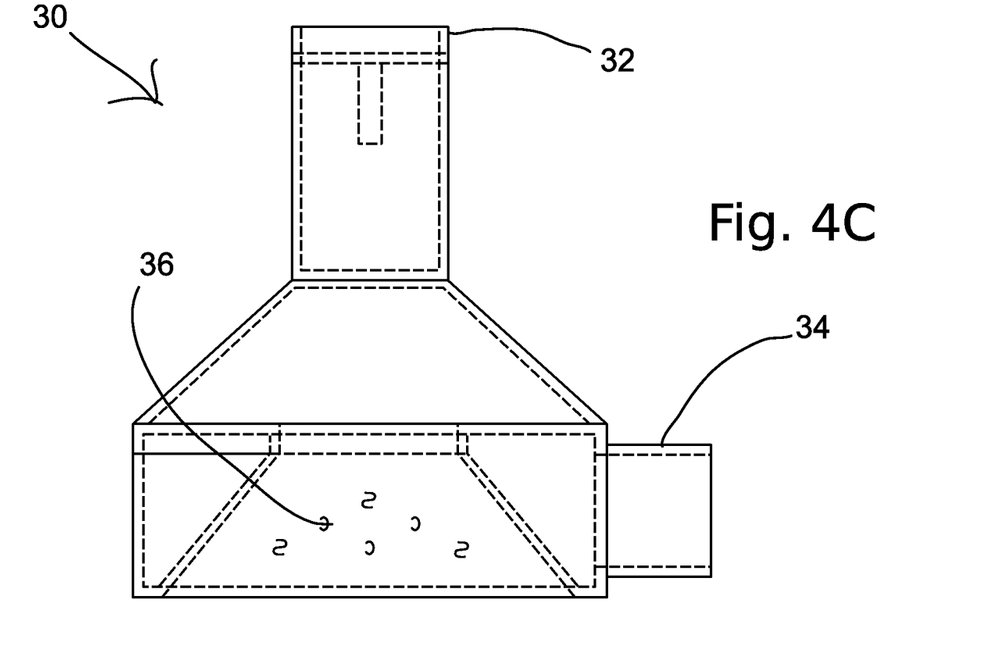
Figure 5:
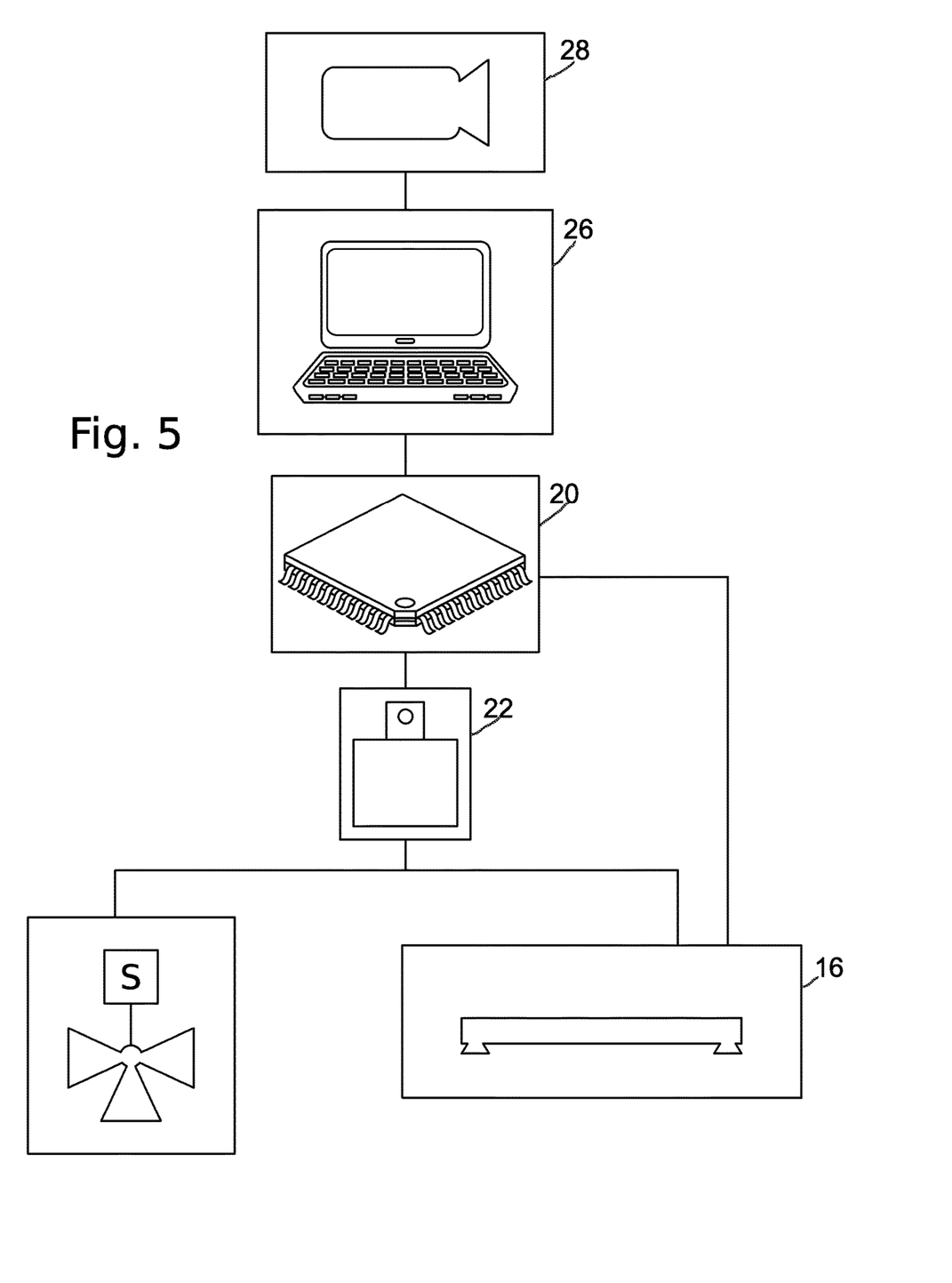
FIG. 5 shows components of the infra-red camera system for measuring blood perfusion.

FIGS. 4A-4C show drawings of the air supply for the IR camera 28, shown in FIG. 5, perfusion system 30 which may be used for thermal cooling of the tissue (not shown). The perfusion system 30 includes the camera mount 32, air supply 34 and air jets 36. FIG. 5 shows components of the infra-red camera system for measuring blood perfusion. The sensor system having an infra-red camera 28, a separate calibration device 20, a means for blowing air 30, a programmed data analysis device 26, and a heater 16.

The Infra-Red Camera should be self-calibrating for surface temperature to insure it gives actual temperature values. It is mounted in a plastic assembly that takes air supplied by a fan or compressor and blows onto the tissue while the surface temperatures are measured. FIG. 4 shows drawings of a preferred design, including holes that form air jets to give high heat transfer coefficients with minimal air flow. An air temperature sensor and air pressure sensors is included close to the outlet of the air jets. The entire assembly including the camera is held in place with a mechanical arm that allows easy positioning relative to the tissue and stability of position once locked in place. The adjoining air calibration system consists of a 15 cm square electric resistance heater sitting on top of a one-inch thick piece of rigid thermal insulation. A controller is used to activate the heater while temperature and heat flux data is recorded from several heat flux sensors mounted onto the heater. The heat flux sensors are made according to US Patent Application No. 27698375, "Heat Flux Gage" filed Dec. 5, 2016, which has been awarded as U.S. Pat. No. 10,393,598 on 27 Aug. 2019.

The sensor system uses a thermal event that is created by the following processes (non-exclusive partial list): Deposition based (screen printing, inkjet printing, 3-D printing, etc.) resistive heater, attached (gluing, pressing, taping, etc.) resistive heater, radiation based heating, induction based heating, fluid based heating, fluid based cooling, gas based heating, gas based cooling, thermoelectric based heating, and thermoelectric based cooling.

The sensor system uses heat flux measurement that can be done using the following (non-exclusive partial list): Heat flux sensors based on ASTM Standard E2684, thermopile based heat flux sensors, and the use of thermocouples in series through a given medium.

The sensor system uses temperature measurement that can be done using the following (non-exclusive partial list), thermocouples, thermistors, infrared temperature measurement, MEMS based temperature sensing, NEMS based temperature sensing, and piezoelectric temperature sensors.

The sensor system uses a data analysis device that can be either wireless based or a wire based.

The air assembly is made of materials that are rigid and easy to machine to give repeatable channels for the air movement and direction to the surface. The goal is to obtain high heat transfer coefficients with the least velocity required.

The mechanical arm positioning system can be of any physical design as long as it is compatible and convenient to hospital and clinic applications. This includes any plastic and metal structures.

It is to be understood that the present invention is not limited to the embodiments described above, but encompasses any and all embodiments within the scope of the following claims.

What is claimed is:

1. A sensor system for measuring blood perfusion and blood temperature of tissue, comprising:
    a sensor system using transient surface heat transfer and temperature measurements of the tissue, and
    having a heat flux sensor, a temperature sensor, an electric resistance heater, and a programmed data analysis device;
    the electric resistance heater provides a thermal event to the tissue, which is to be directly measured by the heat flux sensor and the temperature sensor on a surface of the tissue;
    the programmed data analysis device is programmed to record measurement signals before and during the thermal event provided by the electric resistance heater, as a function of time, and
    use a mathematical thermal model of the tissue to process the measurement signals to determine parameters consisting of the blood perfusion and the blood temperature of the tissue;
    wherein the parameters are determined by matching calculated and measured temperature and heat flux data.

2. A sensor system for measuring blood perfusion and blood temperature using heat transfer and temperature measurements of tissue, comprising:
    a sensor system having an infra-red camera, a separate heat flux calibration device, an air supply with air jets to blow air onto the tissue, and a programmed data analysis device;
    the sensor system uses the infra-red camera to measure transient surface temperature distribution with the air supply air jets to blow air onto the tissue to create a thermal cooling event;
    the separate heat flux calibration device is used to measure a thermal effect of the air blowing on the surface;
    the programmed data analysis device records and uses the measurements before and during the thermal cooling event as a function of time to process the measurements to determine the blood perfusion and the blood temperature of the tissue;
    wherein parameters are determined by matching calculated and measured temperature and heat flux data.

3. The sensor system for measuring blood perfusion and blood temperature of claim 1, wherein:
    the parameters are determined by iteratively matching the calculated and measured temperature and heat flux curves; and
    the mathematical thermal model of the tissue to process the measurement signals to determine the parameters consisting of the blood perfusion and the blood temperature of the tissue and further consisting of thermal contact resistance between the surface and the sensor system.

4. The sensor system for measuring blood perfusion and blood temperature of claim 1, wherein:
    the recorded measurement signals are taken before, during and after the thermal event as a function of time; and
    the mathematical thermal model of the tissue to process the measurement signals to determine the parameters consisting of the blood perfusion and the blood temperature of the tissue, and further consisting of thermal contact resistance between the surface and the sensor system.

5. The sensor system for measuring blood perfusion and blood temperature of claim 4, wherein:

the parameters are determined by iteratively matching calculated and measured temperature and heat flux curves; and the mathematical thermal model of the tissue to process the measurement signals to determine the parameters consisting of the blood perfusion and the blood temperature of the tissue, and further consisting of thermal contact resistance between the surface and the sensor system.

6. The sensor system for measuring blood perfusion and blood temperature of claim 1, wherein:

the recorded measurement signals are taken before, during and after the thermal event as a function of time; and the parameters are determined by iteratively matching calculated and measured temperature and heat flux curves.

7. The sensor system for measuring blood perfusion and blood temperature of claim 1, wherein:

the sensor system is mounted directly on the tissue to create negligible thermal contact resistance, and the parameters are determined by iteratively matching calculated and measured temperature and heat flux curves.

8. The sensor system for measuring blood perfusion and blood temperature of claim 1, wherein:

the parameters are determined by iteratively matching calculated and measured temperature and heat flux curves.

9. The sensor system for measuring blood perfusion and blood temperature of claim 8, wherein:

the sensor system is mounted directly on the tissue to create negligible thermal contact resistance.

10. The sensor system for measuring blood perfusion and blood temperature of claim 2, wherein:

the parameters are determined by iteratively matching calculated and measured temperature and heat flux curves.

11. The sensor system for measuring blood perfusion and blood temperature of claim 2, wherein:

measurement signals are recorded before, during and after the thermal event as a function of time.

12. The sensor system for measuring blood perfusion and blood temperature of claim 2, wherein:

measurement signals are recorded before, during and after the thermal cooling event as a function of time; and the parameters are determined by iteratively matching calculated and measured temperature and heat flux curves.

13. A sensor system for measuring blood perfusion and blood temperature of tissue, comprising:

a sensor system of tissue, and having a heat flux sensor, a temperature sensor, an electric resistance heater, and a programmed data analysis device;

the electric resistance heater provides a thermal event to the tissue, which is to be directly measured by the heat flux sensor and the temperature sensor on a surface of the tissue;

the programmed data analysis device is programmed to record measurement signals before and during the thermal event provided by the electric resistance heater, as a function of time, and use a mathematical thermal model of the tissue to process the measurement signals to determine parameters consisting of the blood perfusion and the blood temperature of the tissue;

wherein the temperature sensor is mounted next to the tissue between the heat flux sensor and the tissue, and the parameters are determined by matching calculated and measured temperature and heat flux data.

14. The sensor system for measuring blood perfusion and blood temperature of claim 13, wherein:

the temperature sensor is flat or a ribbon to maximize contact with the tissue.

15. The sensor system for measuring blood perfusion and blood temperature of claim 13, wherein:

the temperature sensor is a foil thermocouple.

16. The sensor system for measuring blood perfusion and blood temperature of claim 1, wherein:

the heat flux and temperature sensors are covered with a thin plastic layer to isolate electrically and seal from water.

17. The sensor system for measuring blood perfusion and blood temperature of claim 1, wherein:

the temperature sensor is a foil thermocouple mounted next to the tissue between the heat flux sensor and the tissue; and the heat flux and temperature sensors are covered with a thin plastic layer.

* * * * *